United States Patent
Sanberg et al.

(10) Patent No.: US 6,649,160 B1
(45) Date of Patent: *Nov. 18, 2003

(54) SERTOLI CELLS AS TRANSPLANTATION FACILITATOR FOR CELL TRANSPLANTATION

(75) Inventors: Paul R. Sanberg, Springhill, FL (US); Don F. Cameron, Lutz, FL (US); Cesario V. Borlongan, Baltimore, MD (US)

(73) Assignee: University of South Florida, Tampa, FL (US)

( * ) Notice: Subject to any disclaimer, the term of this patent is extended or adjusted under 35 U.S.C. 154(b) by 41 days.

This patent is subject to a terminal disclaimer.

(21) Appl. No.: 09/661,352

(22) Filed: Sep. 14, 2000

Related U.S. Application Data

(63) Continuation of application No. 08/913,864, filed as application No. PCT/US96/03337 on Mar. 12, 1996, now abandoned, which is a continuation-in-part of application No. 08/402,387, filed on Mar. 13, 1995, now Pat. No. 5,830,460.

(51) Int. Cl.[7] ............................................... A01N 63/00
(52) U.S. Cl. ...................... 424/93.7; 424/558; 424/562; 424/570; 424/582
(58) Field of Search .............................. 424/93.1, 93.7, 424/562, 558, 570, 582

(56) References Cited

U.S. PATENT DOCUMENTS

| | | | |
|---|---|---|---|
| 4,829,000 A | 5/1989 | Kleinman et al. | |
| 5,702,700 A | 12/1997 | Sanberg et al. | |
| 5,725,854 A | * 3/1998 | Selawry | 424/93.7 |
| 5,759,534 A | 6/1998 | Selawry | |
| 5,827,736 A | 10/1998 | Heller et al. | |
| 5,830,460 A | 11/1998 | Sanberg et al. | |
| 5,834,001 A | 11/1998 | Dionne et al. | |
| 5,843,430 A | 12/1998 | Selawry | |
| 5,849,285 A | * 12/1998 | Selawry | 424/93.7 |
| 5,858,354 A | 1/1999 | Brinster | |
| 5,869,077 A | 2/1999 | Dionne et al. | |
| 5,871,767 A | 2/1999 | Dionne et al. | |
| 5,874,099 A | 2/1999 | Dionne et al. | |
| 5,942,437 A | 8/1999 | Sanberg et al. | |
| 5,958,404 A | 9/1999 | Selawry | |
| 6,001,643 A | 12/1999 | Spaulding | |
| 6,036,951 A | 3/2000 | Sanberg et al. | |
| 6,037,175 A | 3/2000 | Cameron et al. | |
| 6,083,523 A | 7/2000 | Dionne et al. | |
| 6,149,907 A | 11/2000 | Selawry | |
| 6,322,804 B1 | 11/2001 | Dionne et al. | |
| 2002/0065212 A1 | 5/2002 | Selawry et al. | |
| 2002/0150603 A1 | 10/2002 | Dionne et al. | |

FOREIGN PATENT DOCUMENTS

| | | |
|---|---|---|
| WO | WO 92/06702 A1 | 4/1992 |
| WO | WO 95/28167 A1 | 10/1995 |
| WO | WO 96/28030 A1 | 9/1996 |
| WO | WO 96/28174 A1 | 9/1996 |
| WO | WO 96/33264 A1 | 10/1996 |
| WO | WO 96/40178 A1 | 12/1996 |
| WO | WO 97/33470 A1 | 9/1997 |
| WO | WO 01/66698 A1 | 9/2001 |
| WO | WO 02/063938 A2 | 8/2002 |

OTHER PUBLICATIONS

Koutouzis et al.,"Cell Transplantation for Central Nervous System Disorders", Critical Reviews in Neurobiology, (1994) vol. 8 No. 3 pp 125–162.*

Bellgrau, D. et al., "A role for CD95 ligand in preventing graft rejection" Nature, Oct. 19, 1995, 377:630–632.

Berden et al. "Severe central nervous system toxicity associated with cyclosporine" Lancet 1985, 26:219–220.

Bjorklund and Stenevi "Intracerebral neural grafting: a historical perspective" in Bjorklund, A. and U. Stenevi, eds. Neural grafting in the mammalian CNS, Amsterdam: Elsevier 1985, 3–11.

Bjorklund "Dopaminergic transplants in experimental Parkinsonism: cellular mechanisms of graft–induced functional recovery" Current Opinion in Neurobiology 1992, 2:683–689.

Borlongan et al"Cyclosporine–A increases spontaneous and dopamine agonist–induced locomotor behavior in normal rats" Cell Transplant 1995, 4:65–73.

Byers, S. et al. "Sertoli Cell Junctions and the Seminiferous Epithelium Barrier", pp. 431–446, in The Sertoli Cell, L.D. Russell and M.D. Griswold, Eds, Cache River Press, 1993.

Cameron, D.F. et al. "Formation of Sertoli Cell–Enriched Tissue Constructs Utilizing Simulated Microgravity Technology" Annals New York Acad. Sci., Nov. 2001, 944:420–428.

Cameron, D.F. et al. "Formation of Insulin–Secreting, Sertoli–Enriched Tissue Constructs by Microgravity Coculture of Isolated Pig Islets and Rat Sertoli Cells" In Vitro Cell. Dev. Biol.–Animal, Sep. 2001, 37:490–498.

Cameron, D.F. et al. "Longterm Microgravity Coculture of Sertoli Cells and Islets Enhances Insulin Secretion" Endocrin. Proc., Jun. 15, 1999, P2–230, abstract.

Cameron, D.F. and K.E. Muffly "Hormonal regulation of spermatid binding" J. Cell Sci. 1991, 100:632–633.

Cameron et al. "Successful islet/abdominal testis transplantation does not require Leydig cells" Transplantation 1990, 50:649–653.

Carson, D.D. et al. "Synthesis and Secretion of a Novel Binding Protein for Retinol by a Cell Line Derived from Sertoli Cells" J. Biol. Chem., Mar. 10, 1984, 259(5):3117–3123.

(List continued on next page.)

Primary Examiner—Marianne P. Allen
(74) Attorney, Agent, or Firm—Saliwanchik, Lloyd & Saliwanchik

(57) ABSTRACT

A method of producing a sustained localized immunosuppressive effect in localized tissues is achieved by transplanting Sertoli cells proximate to the tissue.

5 Claims, 7 Drawing Sheets

OTHER PUBLICATIONS

Clermont, Y., "Introduction to the Sertoli Cell", pp. XXI–XXV, in *The Sertoli Cell*, L.D. Russell and M.D. Griswold, Eds, Cache River Press, 1993.

De Cesaris et al., "Inhibition of Lymphocyte Activation by Sertoli Cell Immunosuppressive Factor(s)" Eds–Rivista Di Immunologia ed Immunofarmacologia, 1992, 12(2):86.

De Cesaris, P. et al. "Immunosuppressive Molecules Produced by Sertoli Cells Cultured in vitro: Biological Effects of Lymphocytes" *Biochemical and Biophysical Res. Comm.*, Aug. 14, 1992, 186(3):1639–1646.

De Groen et al. "Central nervous system toxicity after liver transplantation" *N. Engl. J. Med.* 1984, 317(14):861–866.

Djakiew, D. and M. Onoda "Multichamber Cell Culture and Directional Secretion" pp. 181–194, in *The Sertoli Cell*, L.D. Russell and M.D. Griswold, Eds, Cache River Press, 1993.

Dorrington, J.H. et al. "Effects of Follicle–Stimulating Hormone on Cultures of Sertoli Cell Preparations" *Molecular and Cellular Endocrinology*, 1975, 3:57–70.

Free, M.J. et al. "Respiratory Gas Tensions in Tissues and Fluids of the Male Rat Reproductive Tract" *Biology of Reproduction*, 1976, 14:481–488.

Freeman et al. "The USF protocal for fetal nigral transplantation in Parkinson's disease" *Amer. Soc. For Neural Transplantation* 1:29, Abstract, No. 535.

Galdieri, M. et al. "Secretion of Androgen Binding Protein by Sertoli Cells Is Influenced by Contact with Germ Cells" *J. Androl.*, 1984, 5:409–415.

Griswold "Protein secretion by sertoli cells: general considerations" in Russell, L.D. and M.D. Griswold, eds. *The Sertoli Cell*, Cache River Press, Clearwater, FL, 195–200.

Isacson et al. "Graft–induced behavioral recovery in an animal model of Huntington's disease" *Proc. Natl. Acad. Sci.* 1986, 83:2728–2732.

Lejeune, H. et al. "Enhancement of testosterone secretion by normal adult human Leydig cells by co–culture with enriched preparations of normal adult human Sertoli cells" *International J. Andrology*, 1993, 16:27–34.

Lindvall et al. "Transplantation in Parkinson's disease: two cases of adrenal medullary grafts to the putamen" *Ann. Neurol.*, 1987, 22:457–468.

Lindvall et al., "Grafts of fetal dopamine neurons survive and improve motor function in Parkinson's disease" *Science* 1990, 247:574–577.

Ojeifo, J.O. et al. "Sertoli cell–secreted protein(s) stimulates DNA synthesis in purified rat Leydig cell in virto" *J. Reprod. Fert.*, 1990, 90:93–108.

Pakzaban et al. "Increased proportion of Ache–rich zones and improved morphological integration in striatum of fetal grafts . . . " *Exp. Brain Res*, 1993, 97:13–22.

Paxinos and Watson "The rat brain in stereotaxic coordinates" Sydney, Academic Press 1984.

Roberts, K.P. et al. "Immortalization and Characterization of a Sertoli Cell Line from the Adult Rat" *Biology of Reproduction*, 1995, 53:1446–1453.

Sagen, J. et al. "Transplants of immunologically isolated xenogeneic chromaffin cells provide a long–term source of pain–reducing neuroactive substances" *J. Neurosci.* 1993, 13(6):2415–2423.

Sanberg, P.R. et al. "Functional Recovery in Hemiparkinsonian Rats Following Neural Transplantation of Testis–Derived Sertoli Cells" *Soc. For Neurosci.*, Nov. 11–16, 1995, 21:317, abstract 133.12.

Sanberg, P.R. et al. "Sertoli Cells: An Alternative Cell Source for Neural Transplantation in Parkinson's Disease" *Experimental Neurology*, Oct. 1995, 135(2):169 (abstract).

Sanberg, P.R. et al. "Transplantation into the central nervous system" in *Cell Transplantation for Huntington's Disease*, R.G. Landes, Co., Boca Raton, FL, Chap. 4, pp. 19–21, 1994.

Selawry, H.P. and D.F. Cameron "Sertoli cell–enriched fractions in successful islet cell transplantation" *Cell Transplant.* 1993, 2(2):123–129.

Selawry, H.P. et al. "Production of a Factor, or Factors, Suppressing IL–2 Production and T Cell Proliferation by Sertoli Cell–Enriched Preparations" *Transplantation*, Nov. 1991, 52(5):846–850.

Sigma Chemical Company Catalog 1992, pp. 1670–1673.

Skakkebaek, N.E. et al. "Heterotransplantation of Human Foetal Testicular and Ovarian Tissue to the Mouse Mutant Nude" *Acta. Obstet. Gynec. Scand.*, 1975, 53:73–75.

Steinberger, A. and A. Jakubowiak "Sertoli Cell Culture: Historical Perspective and Review of Methods" pp. 155–179, in *The Sertoli Cell*, L.D. Russell and M.D. Griswold, Eds, Cache River Press, 1993.

Steinberger, A. et al. "Isolation and Culture of FSH Responsive Sertoli Cells" *Endocrine Res. Commun.*, 1975, 2(3):261–272.

Verhoeven, G. and J. Cailleau "A factor in spent media from Sertoli cell–enriched cultures that stimulates steroidogenesis in Leydig cells" *Mol. Cell. Endocrinology*, 1985, 40:57–68.

Wictorin et al. "Reformation of long axon pathways in adult rat CNS by human forebrain neuroblasts" *Nature* 1990, 347:556–558.

Welsh, M.J. and J.P. Wiebe "Rat Sertoli Cells: A Rapid Method for Obtaining Viable Cells" *Endocronology*, 1975, 96:618–624.

Whitmore, W.F. et al. "The Role of Germinal Epithelium and Spermatogenesis in the Privileged Survival of Intratesticular Grafts" *The J. Urology*, Oct. 1985, 134:782–786.

Wyatt, C.R. et al. "Suppression of lymphocyte proliferation by proteins secreted by cultured Sertoli cells" *J. Reproductive Immunology*, 1988, 14:27–40.

Korbutt, G.S. et al. "Testicular Sertoli cells exert both protective and destructive effects on syngeneic islet grafts in non–obese diabetic mice" *Diabetologia*, 2000, 43:474–480.

Willing, A.E. et al. "Sertoli cell transplants: their use in the treatment of neurodegenerative disease" *Molecular Medicine Today*, Nov. 1998, 471–477.

Borlongan, C.V. et al. "CNS immunological modulatin of neural graft rejection and survival" *Neurol. Res.*, 1996, 18:297–304.

Sanberg, P.R. et al. "Testis–derived Sertoli cells survive and provide localized immunoprotection for xenografts in rat brain" *Nature Biotechnology*, Dec. 1996, 14:1692–1695.

Sanberg, P.R. et al. "Test–derived Sertoli cells have a trophic effect on dopamine neurons and alleviate hemiparkinsonism in rats" *Nature Medicine*, Oct. 1997, 3(10):1129–1132.

* cited by examiner

SERTOLI CELLS AS TRANSPLANTATION FACILITATOR FOR CELL TRANSPLANTATION

CROSS-REFERENCE TO RELATED APPLICATIONS

This application is a continuation of U.S. patent application Ser. No. 08/913,864, filed Sep. 12, 1997, now abandoned, which is a National Phase filing under 35 U.S.C. §371 of international application No. PCT/US96/03337, filed Mar. 12, 1996, which is a continuation-in-part of U.S. patent application Ser. No. 08/402,387, filed Mar. 13, 1995, now U.S. Pat. No. 5,830,460, all of which are incorporated herein by reference in their entirety.

TECHNICAL FIELD

The present invention relates to methods of transplanting cells to create a localized immunosuppressive and trophic effect in tissue.

BACKGROUND OF THE INVENTION

Transplantation of cells and tissues is being utilized therapeutically in a wide range of disorders including but not limited to from cystic fibrosis (lungs), kidney failure, degenerative heart diseases to neurodegenerative disorders.

As an example, the central nervous system (CNS) (brain and spinal cord) has poor regenerative capacity which is exemplified in a number of neurodegenerative disorders. An example of such a disorder is Parkinson's disease. The preferred pharmacotherapy for Parkinson's disease is L-dopa which helps the symptoms of this disease in humans. However, the neuropathological damage and the debilitating progression is not reversed by this treatment protocol.

Laboratory and clinical studies have shown the transplantation of cells into the CNS is a potentially significant alternative therapeutic modality for neurodegenerative disorders such as Parkinson's disease (Wictorin et al., 1990; Lindvall et al., 1990; Sanberg et al., 1994; Bjorklund and Stenevi, 1985; Freeman et al., 1994). In some cases, transplanted neural tissue can survive and form connections with the CNS of the recipient (i.e. the host) (Wictorin et al., 1990). When successfully accepted by the host, the transplanted tissue,(i.e. the graft) has been shown to ameliorate the behavioral deficits associated with the disorder (Sanberg et al., 1994). The obligatory step for the success of this kind of treatment is the prevention of graft rejection (i.e. graft acceptance).

Currently, fetal neural tissue is the primary graft source for neural transplantation (Lindvall et al., 1990; Bjorklund, 1992; Isacson et al., 1986; Sanberg et al., 1994). Other viable graft sources include adrenal chromaffin cells and various cell types that secrete neural growth factors and trophic factors. The field of neural tissue transplantation as a productive treatment protocol for neurodegenerative disorders has received much attention resulting in its progression to clinical trials. Preliminary results and clinical observations are promising although the graft rejection phenomenon remains a problem.

Recently, studies have suggested that Sertoli cells, when simultaneously transplanted with pancreatic islet cell into the diabetic rat, act as an effective local immunosuppressant on the host tissue (Selawry and Cameron, 1993). As a result, the graft is not rejected and the islets remain viable allowing the transplanted β-cells to function normally and produce insulin for an indefinite period of time. As a result, the accepted graft overcomes the primary physiological dysfunction of hyperglycemia thereby alleviating the related complications of this endocrine disorder. This cell transplantation protocol is accomplished without prolonged systemic immunosuppression, otherwise necessary when islets are transplanted without Sertoli cells.

In general, systemic immunosuppression is necessary if successful transplantation is to be achieved in humans. Immunosuppression of the entire body (i.e. systemic) can result, eventually, in graft acceptance. It is acquired, however, by placing the individual at medical risk making the immunosuppressant therapy itself more of a liability than a benefit in some cases. For a lack of a better immunosuppressant treatment, systemic immunosuppressants, with Cyclosporine-A (CsA) as the treatment choice, have been used as adjunctive therapy in neural and other transplantation protocols (Sanberg et al., 1994; Freeman et al., 1994; Borlongan et al., 1995). Arguably, systemic CsA treatment may be contraproductive to successful graft acceptance in the CNS because of its systemic effect and because CsA itself has been shown to cause detrimental side effects and may, in fact, be cytotoxic to neural tissues (Berden et al., 1985; de Groen et al., 1984).

It would be desirable to enhance the productive cell transplantation techniques already utilized for neurodegenerative disorders, such as Parkinson's disease, in ways which would more effectively slow the neurodegenerative disease process, more actively promote the re-establishment of normal neural tissue physiology and better alleviate the functional disabilities associated with the neural tissue dysfunction. Likewise, it would be desirable to avoid systemic immunosuppression with the ability to locally immunosuppress (i.e. at the graft site) by an immunosuppressant which is biologically tolerated by the host. Sertoli cells may provide this desired option since it is clear from the diabetic studies, as summarized above, that co-transplantation with Sertoli cells will deliver local immunosuppression and promote, therefore, efficient graft acceptance and functional restoration of the tissue-related dysfunction.

SUMMARY OF THE INVENTION AND ADVANTAGES

In accordance with the present invention, there is provided a method of producing a sustained localized immunosuppressive effect and trophic effect in tissue by transplanting Sertoli cells proximate to the tissue.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1A:
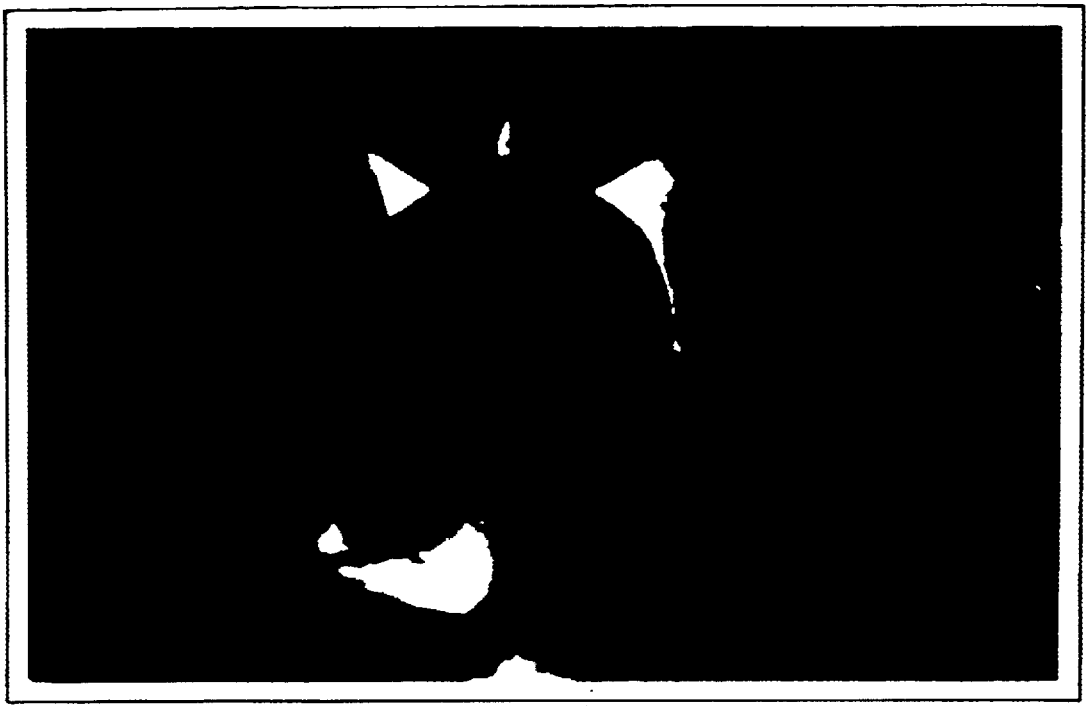
FIGS. 1A–B shows photomicrographs of two representative brain sections wherein the sections were stained with Lectin, the left side of each brain corresponds to the chromaffin cells transplanted side while the right side of each brain corresponds to the chromaffin cells with Sertoli cells the co-transplanted side.

The present invention provides a method of producing a sustained localized immunosuppressive effect and trophic effect in tissue. This is achieved by the general step of transplanting Sertoli cells proximate to the tissue.

By sustained localized immunosuppressive effect, it is meant that the transplanted Sertoli cells will suppress the immunological response ordinarily mounted by the host tissue to the intrusion of foreign entities such as transplanted cells and that the immunosuppression will occur at the graft site (local) rather than by generalized immunosuppression of the entire body (systemic) which occurs with the ordinary methods of immunosuppression by agents such as CsA.

By tissue, it is meant any form of tissue including, but not limited to, cells, blood, organs, and disassociated cells.

In a preferred embodiment, the transplanted cells (which are intended to replace the dysfunctional cells or in some way alleviate tissue dysfunction) can avoid being rejected and thereby survive and functionally integrate into the host tissue. In the CNS, this will promote reestablishment of normal neural tissue function and thereby ameliorate the behavioral and functional deficits associated with the neurological and/or neurodegenerative disorder being treated. However, the method of the present invention can also be utilized with other transplantable cells or tissues other than neural tissue/cells such as endocrine cells, muscle cells, and other cells by utilizing similar techniques as those described for neural cells. Furthermore, the method of the present invention may be used for enhancing the outcomes of tissue and organ transplant, such as lung transplants, by providing localized immunosuppression. That is, Sertoli cells are used to facilitate transplant survival and graft function of the cells being transplanted.

With local immunosuppression by a Sertoli cell-derived immunosuppressant agent (which is now partially characterized), there would be no successful antibody or cellular immunological attack waged against the transplanted cells, including the Sertoli cells themselves. Additionally, since the immunosuppression is local and by a biologically tolerable agent, the side effects associated with both systemic immunosuppression and cytotoxicity of agents such as CsA would be avoided. Hence, the method of Sertoli cell transplantation provides a significant improvement over the use of systemic immunosuppression with CsA as the necessary adjunctive therapy to transplantation as shown in the example below.

The localized immunosuppression by a Sertoli cell-derived immunosuppressant agent can facilitate the survival of both xenografts and allografts. With allografts, co-transplantation with Sertoli cells should provide localized immunosuppression as to eliminate the need for systemic immunosuppression. With xenografts, co-transplantation with Sertoli cells may provide sufficient local immunosupression so as to eliminate the need for systemic immunosupression or the Sertoli cells may be used in combination with a systemic immunosuppressant to prevent rejection thereby reducing the dosage of systemic immunosuppressant required. When co-transplanted, the Sertoli cells not only provide immunosuppression, but provide regulatory, nutritional, and other factors designated as trophic support to the co-transplanted tissue. Therefore, the Sertoli cells will not only provide inhibition of the immune response, but will allow enhanced growth and viability of allografts and xenografts by concomitant trophic support.

The source of Sertoli cells is by primary cell isolation from the mammalian testis. The protocol for harvesting the cells is well-defined (Cameron and Muffly, 1991; Griswold, 1992) and considered a routine methodology. In most of the published reports of Sertoli cell co-transplantation, cells are derived from the rat (Selawry and Cameron, 1993). Although rat Sertoli cells are utilized in the following examples, it is contemplated that the method of the present invention can be used with Sertoli cells from any suitable mammalian source. A preferred source of Sertoli cells for use with mammals, such as humans, are porcine Sertoli cells. However, if available and suitable, human Sertoli cells may be utilized.

In one embodiment, the Sertoli cells are co-transplanted with the selected neural tissue or other appropriate tissue into the CNS by intracranial infusion (Sanberg et al., 1995).

By proximate to the tissue, it is meant that the Sertoli cells are placed in general proximity to the selected tissue such as the neural tissue. Generally, this means that the Sertoli cells can be infused or transplanted into any mammal so as to become located in proximity to the selected tissue. For example, the location can be any site where there is neural tissue such as the CNS, PNS, or fluids which bathe neural tissue such as cerebral spinal fluid and blood, blood vessels, or other tissues which are enervated such as endothelial tissue, muscle tissues, end organs, etc. The proximity of the Sertoli cells to the neural tissue is determined by the specific neural cells and function sought to be restored in a given transplantation. Additionally, in transplants involving non-neural tissue, the proximity of the Sertoli cells is determined by the specific tissue being transplanted.

The source of neural cells for transplantation depends on the neurological disorder being treated. For example, Parkinson's disease is treated with ventral mesencephalic tissue (Lindvall et al., 1990) or chromaffin cells (Lindvall et al., 1987), Huntington's disease is treated with striatal lateral eminence cells (Isacson et al., 1986) and neurological pain is treated with adrenal chromaffin cells (Sagen et al., 1993). Other tissue types experimentally transplanted into specific animal models of human neurodegenerative disorders are summarized elsewhere (Dunnett and Bjorklund, 1994) and provide detailed descriptions of cell isolation and transplantation methods. Other non-neural tissues that have been transplanted are generally reviewed elsewhere (Sanberg, 1992) and provide detailed descriptions of cell isolation and transplantation methods.

The present invention also teaches a method of producing a sustained localized immunosuppressive effect in a target tissue by transplanting porcine Sertoli cells into the tissue. For example, transplanting porcine Sertoli cells into the central nervous system (CNS) of a subject, the cells secreting trophic factors in situ, for treating neurological disorders including epilepsy, stroke, Huntington's disease, head injury, spinal injury, pain, Parkinson's disease, myelin deficiencies, muscular dystrophy and other neuromuscular disorders, neurological pain, amyotrophic lateral sclerosis, Alzheimer's disease, and affective disorders of the brain.

The following examples demonstrate the methods of use of the present invention as well as efficacy for producing a sustained localized immunosuppressive effect.

EXAMPLE 1

Materials and Methods

Sprague-Dawley male rats, six weeks old, which were obtained from Harlan Sprague-Dawley, Inc. (Indianapolis, Ind.), were used. The animals were housed in individual Plexiglas cages in a room with controlled humidity and temperature and under a 12 hour light-dark cycle. Food and water were freely available ad lib.

Cell Culture

Bovine chromaffin cells were obtained from the laboratory of Dr. Jaqueline Sagen at the Univer sity of Chicago at Illinois. Upon arrival, cells were plated using DMEM-F12 media with serum. Cell counts using the tryphan blue method revealed a total of $8 \times 10^{-6}$ per ml of surviving cells. A 95% viability of chromaffin cells were measured at the day of arrival and during the day of transplantation. Half of the chromaffin cells solution was co-cultured overnight with Sertoli cells.

The preparation of Sertoli cells is according to the method described by Selawry & Cameron (Selawry and Cameron, 1993), which is incorporated herein by reference. Specifically, the testes were removed, chopped into several pieces, and placed in a 50 ml conical tube containing 50 ml of Ham's F12/DMEM media. The pieces were washed once by centrifugation at 800×g for two minutes. The supernatant was aspirated, and the tissue resuspended in 40 ml of media containing 40 mg trypsin and 0.8 mg DNase in a sterile 250 ml Erlenmeyer flask. The flask was placed in an 37° C. oscillating incubator at 60–90 osc/minutes for 30 minutes. This step removed Leydig cells.

The tubules were then transferred to a 50 ml conical tube, and centrifuged at 800×g for two minutes. The supernatant fraction was aspirated, and the pellet resuspended in 40 ml of 1 M glycine, 2 mM EDTA containing 0.01% soybean trypsin inhibitor and 0.8 mg DNase, and incubated at room temperature for ten minutes. This step lysed any residual Leydig cells. The cells were washed by centrifugation for two minutes, and the step repeated twice, or until the media was no longer cloudy. The pellet was resuspended by gentle homogenization with a glass Pasteur pipet in 40 ml of media containing 20 mg collagenase in an Erlenmeyer flask, and incubated at 37° C. for five minutes with 60–90 osc/minutes.

The cell suspension was centrifuged at 800×g for two minutes, and the pellet was resuspended by gentle homogenization with a Pasteur pipet in 40 ml media containing 40 mg collagenase and 0.2 mg DNase, and incubated in an Erlenmeyer flask at 37° C. for 30 minutes with 60–90 osc/minutes. The cells were then washed by centrifugation for two minutes, and the process repeated at least three times to eliminate peritubular cells. The cells were resuspended by gentle homogenization with a Pasteur pipet in 40 ml media containing 40 mg hyaluronidase and 0.2 mg of DNase, and incubated at 37° C. for 30 minutes with 60–90 osc/min. The cells were pelleted by soft centrifugation for two minutes, and washed at least five times to eliminate germ cells.

The resultant Sertoli cell-enriched fraction was resuspended into 0.25 ml of media with the chromaffin cells for at least 24 hours before transplantation. During the day of transplantation, the solution containing the Sertoli cell-enriched fraction and the chromaffin cells were resuspended using a Pasteur pipet then suctioned by a Hamilton syringe with a spinal needle of gauge 20.

Surgery

The surgical procedures were carried out in sterile conditions, as is well known in the art (Pakzaban et al., 1993). All animals were initially anesthetized with 0.60 ml/kg of sodium pentobarbital, then placed in Kopf stereotaxic instrument. Bilateral striatal transplants were performed with coordinates set at: anterioposterior =+1.2, medialateral=+/−2.8; dorsoventral −6.0, 5.9 & 5.8 (based on the atlas of Paxinos and Watson, 1984). The right hemisphere of the brain was transplanted with bovine chromaffin cells while the left hemisphere received chromaffin cells plus Sertoli cells. Each side received a total volume of 3 $\mu$l of the cell cocktail solution (1 $\mu$l per DV site). After surgery, the animals were placed on heating pads until recovery. Animals received a short course of immunosuppression using Cyclosporine-A (20 mg/kg/d,i.p.) immediately after surgery and on the day following the transplant. All animals were sacrificed at one month post transplant.

Histology

Animals were anesthetized with 0.70 ml/kg of sodium pentobarbitol, then perfused with 500 ml of 0.9% isotonic saline and 500 ml paraformaldehyde. The animals were then decapitated, and the brain removed and post-fixed overnight in 40% paraformaldehyde with 30% sucrose in PBS. The following day, brain sections were cut at 30 microns using the Vibroslice (Campden Instrument, UK). Host tissue immunologic response was analyzed using the Lectin method (see below). Three experimenters conducted independent qualitative comparisons of the left and right side of the brain in a blind-randomized manner.

Lectin Method

Following vibrotome sectioning, brain sections were placed in 0.1% Triton X-100 for 15–30 minutes. The sections were then washed in 0.1M cationic PBS(pH 7.2), containing 0.1 mM $CaCl_2$, 0.1 mM $MgCl_2$. Incubation of sections was carried out in 20.0 $\mu$g/ml lectin made in cationic PBS at 4° C. for two hours. Rinsing, three times in PBS was done prior to incubation with DAB. The DAB stock solution was made by dissolving 10 mg DAB in 20 ml phosphate buffer (0.1 M, pH 7.2) and adding 0.5 ml of 1% $CoCl_2$ to DAB solution while stirring. Sections were first preincubated in DAB solution for 15 minutes. Upon adding 0.6 ml 3% $H_2O_2$ to 20.5 ml DAB solution, incubation lasted for five to ten minutes or until appropriate reaction was reached. Sections were again rinsed three times in PBS. Finally, sections were mounted from distilled water to wash out salts.

RESULTS

Figure 1B:
Figure 2A:
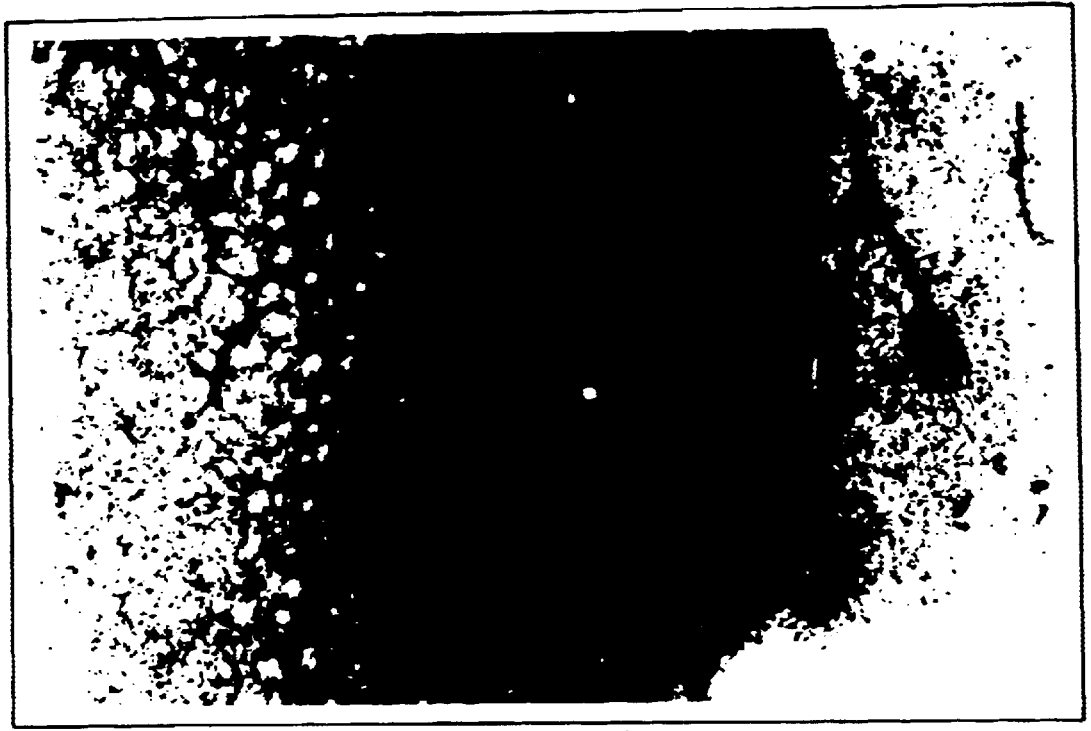
FIGS. 2A–D show a higher magnification from the photomicrograph of FIG. 1 of the transplant sites of brain sections illustrated in FIG. 1; panels A and C show the chromaffin cells transplanted side while panels B and D show the side co-transplanted chromaffin cells with Sertoli cells.
Figure 2B:
Figure 2C:
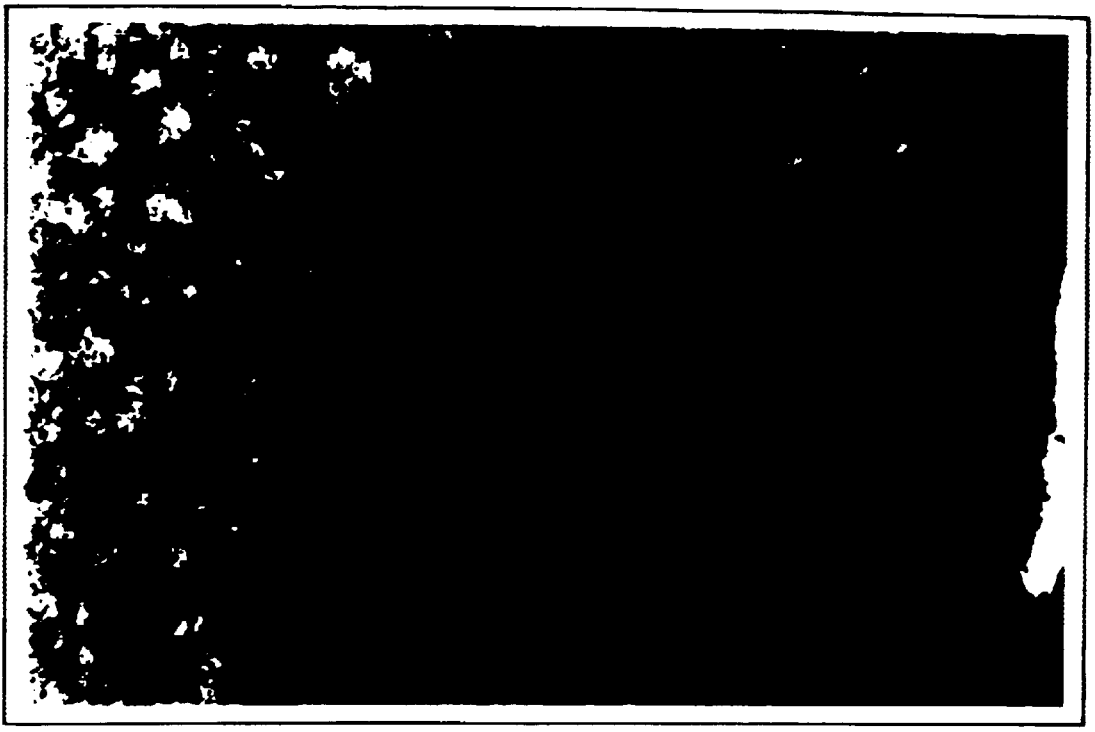
Figure 2D:
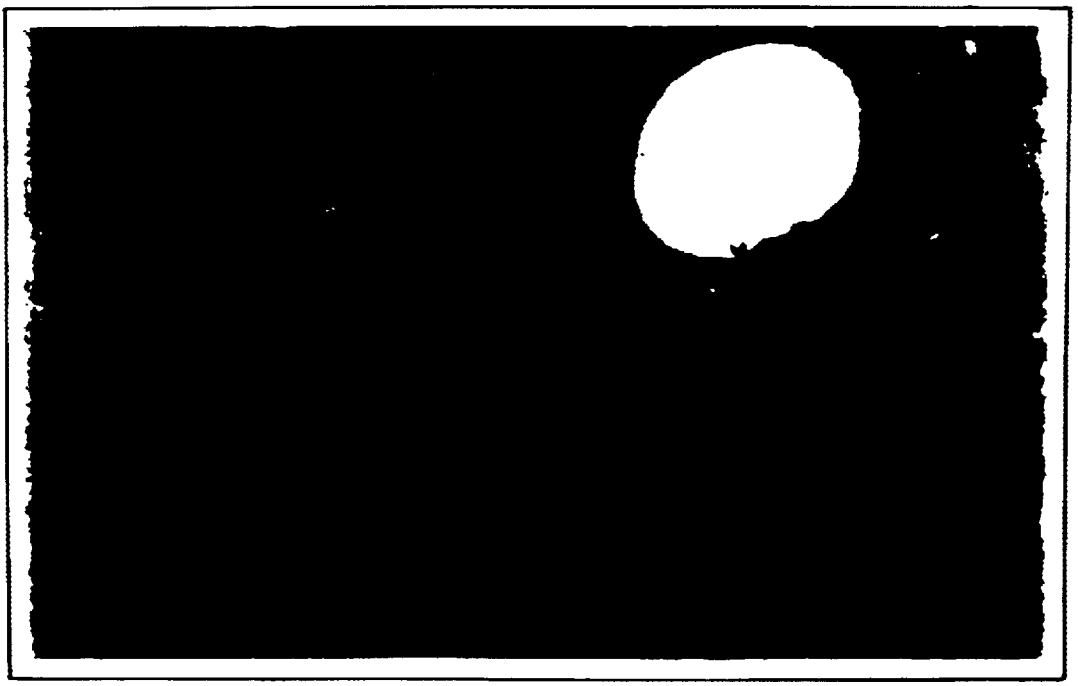

Histological analyses of both transplant sites revealed that the transplanted side with chromaffin cells alone had greater glial infiltration and higher number of macrophages than the transplanted side with chromaffin cells plus Sertoli cells (FIGS. 1 & 2). No significant difference in glial response was observed between animals treated with or without cyclosporine.

Two conclusions are made from the data: 1) a localized effect of the Sertoli cells which appeared to suppress the immune response of the host tissue to the transplanted cells, and 2) a sustained immunosuppression, with or without a short course of CsA administration, can be achieved with simultaneous transplantation of chromaffin cells with Sertoli cells (FIG. 4).

It can therefore be concluded that Sertoli cells can provide an immunologically privileged site in the CNS by direct intracranial infusion. Furthermore, with significant immunosuppression obtained following xenografts in the present study, Sertoli cells can provide greater beneficial effects on creating immunologically privileged sites following allografts, and enhance survival and integration of the transplant through immunological and trophic support.

EXAMPLE 2

Specific Protocol: The protocol involves three basic steps, Sertoli cell isolation, co-culture with neural specific cells or other appropriate cells and transplantation of the co-culture into the CNS (for details regarding the cell isolation see Selawry and Cameron (1993) and for details regarding cell transplantation see (Pakzaban et al., 1993).

1A. Sertoli Cell Isolation

The isolation procedure follows a well-defined method as described in reference (Selawry and Cameron, 1993). The cell culture medium used in all isolation steps and in which the cells were incubated was DMEM:Hams F12 supplemented with retinol, ITS and gentamicin sulfate (Cameron and Muffly, 1991). Testes were surgically collected from sixteen day old male Sprague-Dawley rats. The testes were decapsulated and prepared for enzymatic digestion to separate other testicular cell types from the Sertoli cells. The enzymatic procedure using collagenase (0.1%), hyaluronidase (0.1% and trypsin (0.25%) is routinely used in many cell isolation protocols. After sequential enzymatic digestion, the Sertoli cell isolate was washed with culture medium, transferred to sterile cell culture vessels and placed in a humidified, 5% $Co_2$-95% air tissue culture incubator. Following forty-eight hours of pre-incubation in a 39° C. incubator, the Sertoli cells were washed to remove any contaminating debris. The resultant Sertoli cell-enriched fraction was resuspended into 0.25 ml of DMEM/F12 medium, and incubated at 37° C. for at least 24 hours.

The Sertoli cells were liberated from the vessel floor with 0.01% trypsin, transferred to a sterile conical test tube and repeatedly washed by centrifugation and then treated with trypsin inhibitor to cease the enzymatic action of trypsin. During the day of transplantation, the Sertoli cell-enriched fractions are resuspended and suctioned by a Hamilton syringe with a twenty gauge spinal needle.

1B. Isolation and Pretreatment of Sertoli Cells

As previously described (Cameron and Muffly, 1991) decapsulated rat testes were subjected to sequential enzymatic treatment at 37° C. using 0.25% trypsin (Sigma) and 0.1% collagenase (Sigma, type V) (Cameron and Muffly, 1991). The resulting Sertoli cell aggregates were equally distributed in a volume of 20 ml incubation medium into 75 $cm^2$ tissue culture flasks (Costar). Plated Sertoli aggregates were incubated at 39° C. 5% $CO_2$-95% air for 48 hours after which cells were subjected to hypotonic treatment with sterile 0.5 mM Tris-HCl buffer for one minute (Galdieri et al. 1981) to expedite the removal of contaminating germ cells. Following two washes with incubation medium, flasks were replenished with 20 ml incubation medium and returned to the $CO_2$-injected incubator at 37° C. in 5% $CO_2$-95% air. The resulting pre-treated Sertoli-enriched monocultures contained greater than 95% Sertoli cells. Plating density (<$2.0\times10^6$ Sertoli cells/$cm^2$) did not result in aconfluent monolayer of cells.

2. Co-Culture With Neural Specific Cells

Sertoli cells and neural cell specific for transplantation for the neurodegenerative model were suspended by trypsin (0.01%), washed three times with medium and placed into a sterile cell culture vessel twenty-four hours prior to transplantation. The resulting co-culture was placed in a 5% $CO_2$-95% air incubator at 37° C. until utilized for transplantation.

3. Transplantation of Co-Culture Into the CNS

The transplantation protocol follows the procedure as previously described by Pakzaban et al., (1993). The animal surgery was carried out in sterile conditions. All animals were initially anesthetized with 0.60 ml/kg sodium pentobarbital, then placed in a Kopf stereotaxic instrument. For the Parkinson's disease model, unilateral striatal transplants are performed with coordinates set at: anterioposterior—+1.2, mediolateral—+/−2.9, dorsoventral—6.0, 5.9 and 5.8 (based on the atlas of Paxinos and Watson) (1984). Different coordinates are used for different neurodegenerative animal models also based on Paxinos and Watson (1984). The striatum ipsilateral to the lesioned substantia nigra is transplanted with Sertoli cells or with the Sertoli cell co-culture. Each striatum receives a total volume of 3 μl of Sertoli cell or co-culture suspension. One microliter of the cell suspension was infused over one minute per dorsoventral site. Another five minutes was then allowed upon reaching the last dorsoventral site before retracting the needle. After surgery, the animals were placed on heating pads until they recovered. The animals received a short course of immunosuppression therapy using Cyclosporine-A (20 mg/kg/d, i.p.) immediately after surgery and on the day following the transplant.

Sertoli cells and/or co-culture suspensions are transplanted into animal models of various neurodegenerative disorders by stereotaxic coordinates defined for the specific disorder, as illustrated in the Parkinson's disease example. All experimental animals are systematically assayed for functional recovery by techniques specific to that animal model.

EXAMPLE 3

Figure 4A:
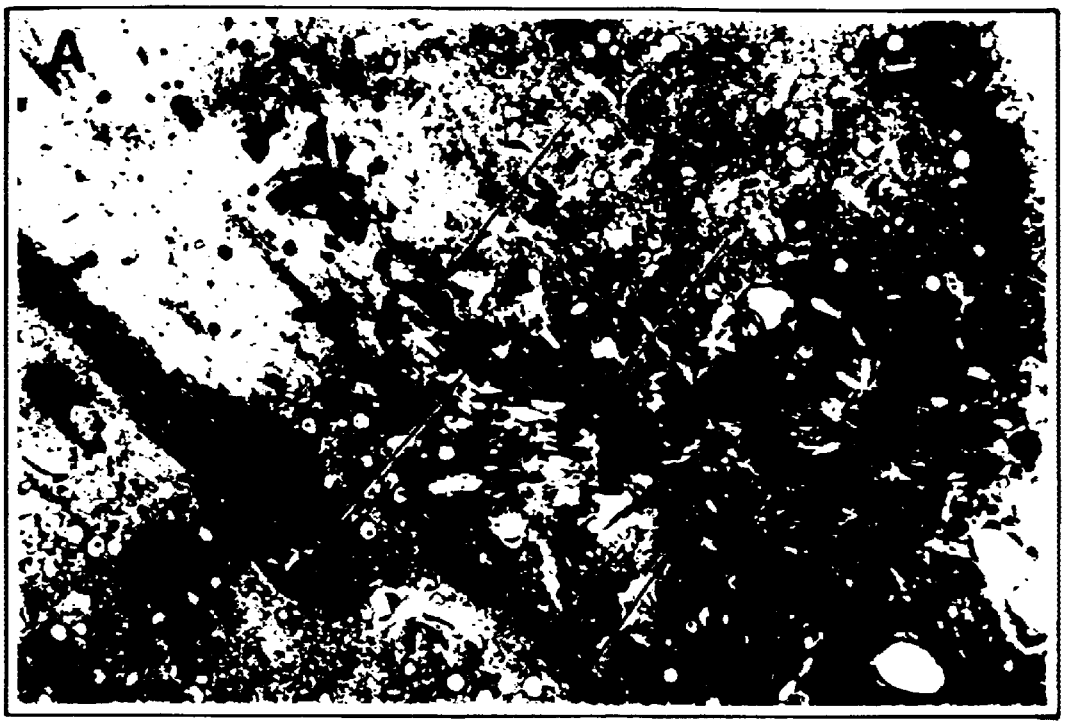
FIGS. 4A–B are electron micrographs illustrating the cellular structure and tissue architecture of the Sertoli cell/chromaffin cell co-grafts in the striatum of the brain, wherein (A) depicts electron dense chromaffin cells (arrows) easily identified because of the inclusion of secretory granules unique to these cells, and (B) shows the boxed area in (A) at higher magnification, with higher resolution, Sertoli cells (arrows) are seen immediately adjacent to the electron dense chromaffin cells.
Figure 4B:

FIG. 4A illustrates that electron dense chromaffin cells (arrows) were easily identified because of the inclusion of secretory granules unique to the cells. FIG. 4B shows the boxed area in FIG. 4A at a higher magnification, wherein at a higher resolution, Sertoli cells (arrows) were detected immediately adjacent to the electron dense chromaffin cells. This demonstrates the survival of co-grafted adrenal chromaffin cells with Sertoli cells in the brain.

(1) Growth of Neural Cells
Incubation Medium and Sertoli Cell Pre-Conditioned Medium:

The incubation medium used for Sertoli cell culture and co-culture was Dulbecco's Minimum Essential Medium: Hams F12 Nutrient Medium (Whittaker Bioproducts) mixed 1:1 and supplemented with 3 mg/ml L-glutamine (Sigma, grade III), 0.01 cc/ml insulin-transferrin-selenium (ITS, Collaborative Research, Inc.), 50 ng/ml retinol (Sigma), 19 $\mu$l/ml lactic acid (Sigma) and 0.01 cc/ml gentamicin sulfate (Gibco).

Following the first 48 hour incubation period of isolated Sertoli cells, media was collected and centrifuged at 1500 rpm for five minutes. The supernatent was collected and immediately frozen in sterile test tubes. This medium was identified as Sertoli pre-conditioned medium (SCM).
Isolation and Incubation of Fetal Brain Cells:

Fetal brain cells (FBC) were collected from the ventral mesencephalon of fetal rats (15–17 days gestation). The fetal brain tissue was suspended in medium and initially dispersed by passing it through a series of sequentially decreasing sized hypodermic needles (18–26 gauge). The resulting suspension was treated with 0.1% trypsin for five minutes and followed by 0.1% trypsin inhibitor for two minutes. The suspended FBC were washed (three times), resuspended in incubation medium and plated in poly-L-lysine-coated culture vessels.

Figure 3A:
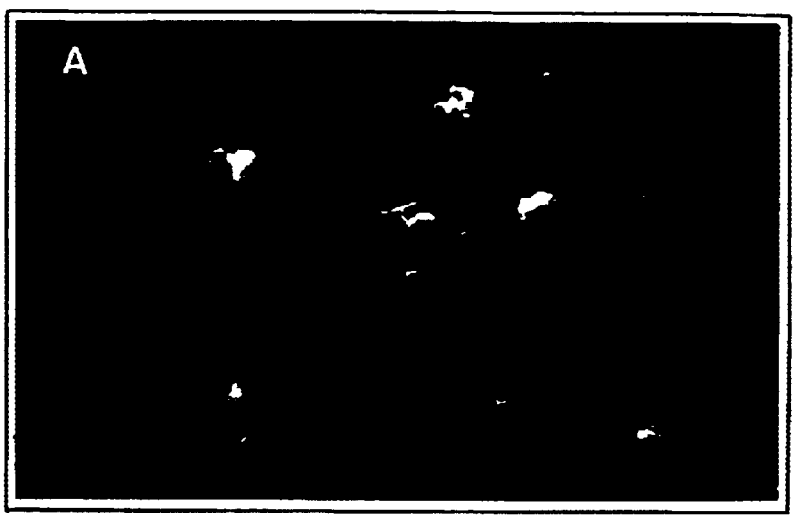
FIGS. 3A–C are light micrographs illustrating cells from the ventral mesencephalon of fetal rats (VM) isolated and cultured for seven days in control medium (CM) or Sertoli cell pre-conditioned medium (SCM) and photographed with darkfield, interference contrast optics, wherein (A) depicts VM cells incubated in CM showing no evidence of stimulation or differentiation, (B) depicts VM cells incubated in SCM appearing highly stimulated, and (C) at higher magnification, depicts VM cells incubated in SCM exhibiting neurite outgrowth.
Figure 3B:
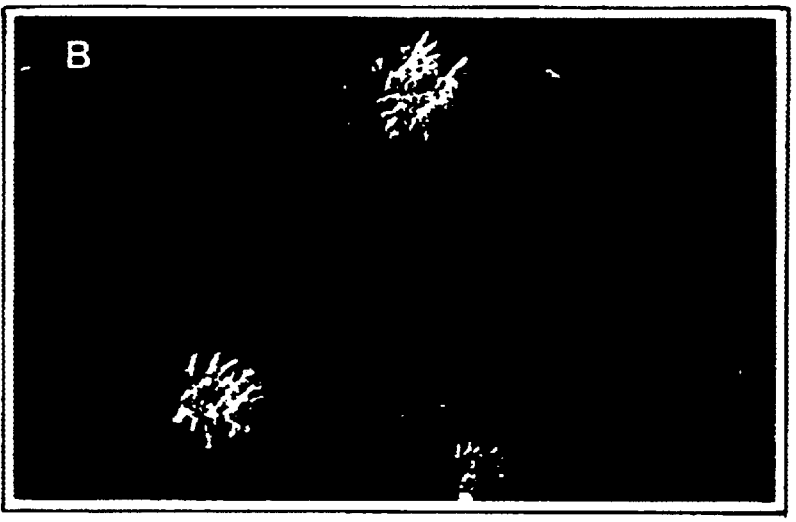
Figure 3C:
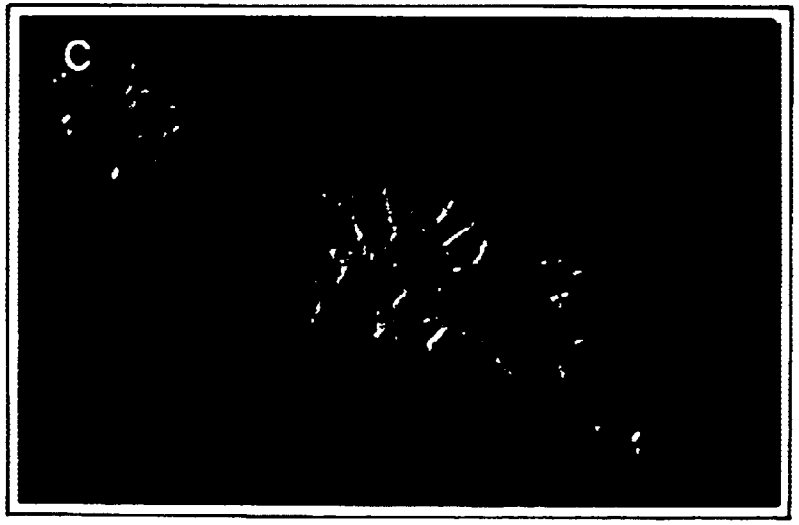

Cells from the ventral mesencephalon of fetal rats (VM) were isolated and cultured for seven days in control medium (CM) or Sertoli cell pre-conditioned medium (SCM) as shown in FIG. 3A, VM cells incubated in CM showed no evidence of cellular stimulation or differentiation. Referring to FIG. 3B, VM cells incubated in SCM were highly stimulated. FIG. 3C illustrates that at higher magnification, VM cells incubated in SCM show neurite outgrowth.

EXAMPLE 4

Incorporation of Latex Beads:

Sertoli cells were isolated and prepared for incubation as described. Prior to transplantation (approximately 12 hours), sterile 1 $\mu$m latex beads (10 $\mu$l/ml medium; Pelco, Tustin, Calif.) were added to the incubation medium. Sertoli cells rapidly phagocytosed the beads. Immediately prior to transplantation, the beaded Sertoli cells were washed (three times) and resuspended in 1 ml of incubation medium.

Figure 5A:
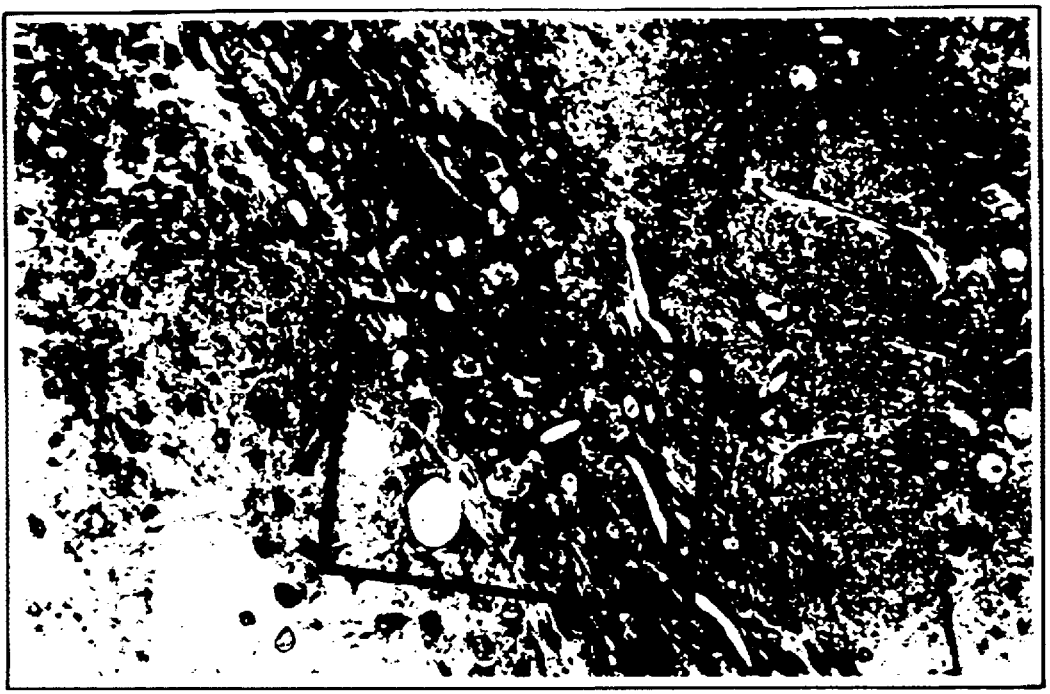
FIGS. 5A–B are electron micrographs illustrating (A) the striatum of the brain shows the penetration tract (arrows) and the site of Sertoli cell transplantation, and (B) shows the boxed area in (A) at higher magnification, with higher resolution, Sertoli cells (arrows) are easily identified because of the 1$\mu$ latex bead inclusions which were loaded into the cells prior to transplantation.
Figure 5B:
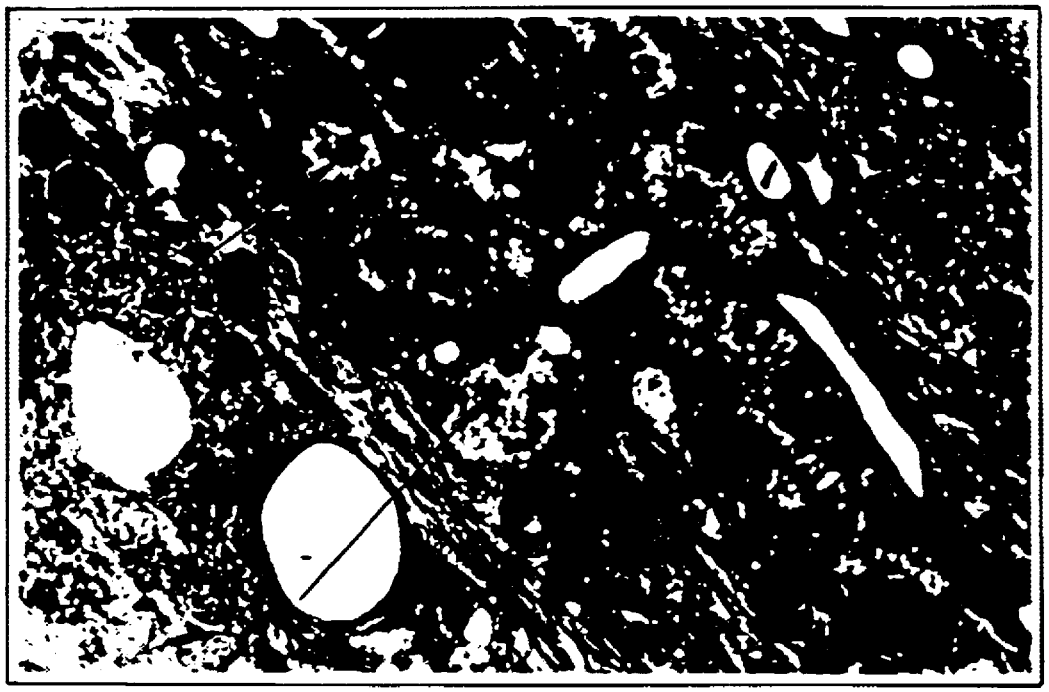

Referring to FIG. 5A, Sertoli cells were transplanted into the striatum of the brain wherein the penetration tract (arrows) and the site of Sertoli cell transplantation are shown. At higher magnification as shown in FIG. 5B, Sertoli cells (arrows) were easily identified because of the inclusion of 1$\mu$ latex beads which were loaded into the Sertoli cells prior to transplantation.

EXAMPLE 5

Effects of Cyclosporine A (CsA) on the Survival of Transplanted Sertoli Cells

Fluorescent cell labeling: Immediately prior to transplantation (approximately two hours), Sertoli cell monocultures were treated with CM-DiI fluorescent dye for cell tracking (100 $\mu$l stock/ml medium; Molecular Probes, Inc., Eugene, Oreg.) for 7 minutes at 37° C. and then placed in the refrigerator (4° C.) for an additional 15 minutes. Fluorescent "tagged" Sertoli cells were washed (three times) and resuspended in 1 ml of incubation medium.

Figure 6A:
FIGS. 6A–B are two light micrographs illustrating grafted Sertoli cells in situ labeled with a florescent tag (DiI) prior to their transplantation into the striatum of the brain wherein (A) depicts viable, florescent Sertoli cells in a rat host that had not received immunosuppression therapy with Cyclosporine A (CsA), and (B) shows viable, florescent Sertoli cells in the rat host that had received cyclosporine A immunosuppression therapy.
Figure 6B:
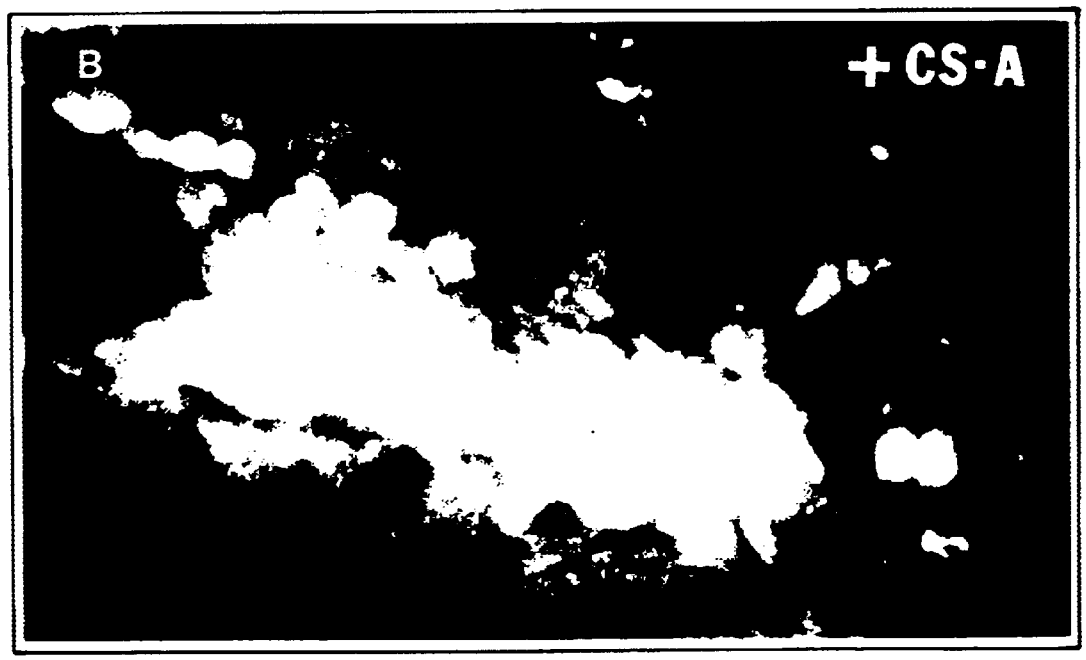

The effect of cyclosporine A on the survival of grafted Sertoli cells in situ was examined. Grafted Sertoli cells were labeled with a fluorescent tag (DiI) prior to transplantation into the striatum of the brain. The tissue was collected one month post-transplantation. Referring to FIG. 6A, viable fluorescent Sertoli cells were seen in a rat host that had not received immunosuppression therapy with cyclosporine A. Referring to FIG. 6B, viable fluorescent Sertoli cells are shown in a rat host that had not received cyclosporine A immunosuppression therapy. This example demonstrates that cyclosporine A is not necessary for the survival of Sertoli cells transplanted into the brain.

Throughout this application various publications are referenced by citation. Full citations for the publication are listed below. The disclosure of these publications in their entireties are hereby incorporated by reference into this application in order to more fully describe the state of the art to which this invention pertains.

The invention has been described in an illustrative manner, and it is to be understood the terminology used is intended to be in the nature of description rather than of limitation.

Obviously, many modifications and variations of the present invention are possible in light of the above teachings. Therefore, it is to be understood that within the scope of the appended claims, the invention may be practiced otherwise than as specifically described.

REFERENCES CITED

Berden et al., "Severe central nervous system toxicity associated with cyclosporine" Lance 26:219–220 (1985).
Bjorklund and Stenevi, "Intracerebral neural grafting: a historical perspective" in Bjorklund, A. and U. Stenevi, eds. Neural grafting in the mammalian CNS, Amsterdam: Elsevier, 3–11 (1985).
Bjorklund, "Dopaminergic transplants in experimental Parkinsonism: Cellular mechanisms of graft-induced functional recovery" Current Biology, 2:683–689 (1992).
Borlongan et al., "Cyclosporine-A increases spontaneous and dopamine agonist-induced locomotor behavior in normal rats" Cell Transplant., 4:65–73 (1995).
Borlongan et al. "PR: Systemic 3-nitropropionic acid: Behavioral deficits and striatal damage in rats", Brain Research Bulletin, 036:549–556 (1995).
Cameron et al., "Successful islet/abdominal testis transplantation does not require Leydig cells" Transplantation, 50:649–653 (1990).
Cameron and Muffly, "Hormonal regulation of spermated binding to Sertoli cells in vitro" J. Cell Sci., 100:532–533 (1991).
de Groen et al., "Central nervous system toxicity after liver transplantation" N. Engl. J. Med. 14:861–866 (1984).
Dunnett and Bjorklund, Functional Neural Transplantation, Advances in Neuroscience, Volume 2, Raven Press, New York.
Freeman et al., "The USF protocol for fetal nigral transplantation in Parkinson's disease" Experimental Neurology, 129:6–7 (1994).
Griswold, "Protein secretion by Sertoli cells: general considerations" in Russel, L. D. and M. D. Griswold, eds. The Sertoli Cell, Cache River Press, Clearwater, Fla., 195–200.
Isacson et al., "Graft-induced behavioral recovery in an animal model of Huntington's disease" Proc. Natl. Acad. Sci., 83:2728–2732 (1986).

Koutouzis et al., "PR: Systemic 3-nitropropionic acid: Long term effects on locomotor behavior" *Brain Research*, 646:242–246 (1994).

Lindvall et al., "Transplantation in Parkinson's disease: two cases of adrenal medullary grafts to the putamen" *Ann. Neurol.*, 22:457–468 (1987).

Lindvall et al., "Grafts of fetal dopamine neurons survive and improve motor function in Parkinson's disease" *Science*, 247:574–577 (1990).

Pakzaban et al., "Increased proportion of Ache-rich zones and improved morphological integration in host striatum of fetal grafts derived from the lateral but not the medial ganglionic eminence" *Exp. Brain Res.*, 97:13–22 (1993).

Paxinos and Watson, "The rat brain in stereotaxic coordinates" Sydney, Academic Press (1984).

Sagen et al., "Transplants of immunologically isolated xenogeneic chromaffin cells provide a long-term source of pain-reducing neuroactive substances" *J. Neurosci.* 13:2415–2423 (1993).

Sanberg, PR. (Editor-in-chief) "Cell Transplantation", *Elservie Science* Publishers, New York, 1992-Present Sanberg et al., "Cell transplantation for Huntington's disease" R. G. Landes Co., Boca Raton, Fla., pp. 19–21 (1994).

Sanberg et al., "Sertoli cells induce immunoreactivity and functional recovery following transplantation into the striatum of 6-OHDA lesioned rats (in preparation) (1995).

Selawry and Cameron, "Sertoli cell-enriched fraction in successful islet cell transplantation" *Cell Transplant.*, 2:123–129 (1993).

Wictorin et al., "Reformation of long axon pathways in adult rat CNS by human forebrain neuroblasts" *Nature*, 347:556–558 (1990).

What is claimed is:

1. A method of producing a sustained localized immunosuppressive effect in target tissue with a mammal, said method comprising co-transplanting Sertoli cells and neural cells to the target tissue, wherein the neural cells are first co-cultured with the Sertoli cells and wherein the co-cultured trasplant cells and Sertoli cells are co-transplanted together to the target tissue.

2. A method of producing a sustained localized immunosuppressive effect in neural tissue within a mammal, said method comprising co-transplanting Sertoli cells and neural cells to the neural tissue, wherein the neural cells are first co-cultured with the Sertoli cells and the co-cultured neural cells and Sertoli cells are co-transplanted together to the neural tissue.

3. A method of producing a sustained localized immunosuppressive effect in neural tissue within a mammal suffering from a neurological disorder, said method comprising co-transplanting Sertoli cells and neural cells to the neural tissue, wherein the neural cells are first co-cultured with the Sertoli cells and the co-cultured neural cells and Sertoli cells are co-transplanted together to the neural tissue.

4. The method according to claim 3, wherein the neurological disorder is a neurodegenerative disorder.

5. The method according to claim 3, wherein the neurological disorder is selected from the group consisting of Huntington's disease, Parkinson's disease, and neurological pain.

* * * * *

UNITED STATES PATENT AND TRADEMARK OFFICE
CERTIFICATE OF CORRECTION

PATENT NO.      : 6,649,160 B1
DATED           : November 18, 2003
INVENTOR(S)     : Paul R. Sanberg, Don. F. Cameron and Cesario V. Borlongan It is certified that error appears in the above-identified patent and that said Letters Patent is hereby corrected as shown below:

Column 11,
Line 21, "Elservie Science Publishers, New York, 1992-Present Sanberg..." should read -- Elservie Science Publishers, New York, 1992-Present (this reference ends) (Begins new line and new reference begins) Sanberg, PR.... --

Column 12,
Line 2, "A method of producing a sustained localized immunosuppressive effect in target with a mammal, said method comprising co-transplanting Sertoli cells and neural cells to the target tissue, wherein the neural cells are first co-cultured with the Sertoli cells and wherein theco-cultured transplant cells and Sertoli cells are co-transplanted together to the target tissue." should read -- A method of producing a sustained localized immunosuppressive effect in target tissue within a mammal, said method comprising co-transplanting Sertoli cells and transplant cells to the target tissue, wherein the transplant cells are first co-cultured with the Sertoli cells, and wherein the co-cultured transplant cells and Sertoli cells are co-transplanted together to the target tissue. --

Signed and Sealed this

Third Day of August, 2004

JON W. DUDAS
*Acting Director of the United States Patent and Trademark Office*